US011147496B2

(12) United States Patent
Ghodrati et al.

(10) Patent No.: US 11,147,496 B2
(45) Date of Patent: Oct. 19, 2021

(54) SYSTEMS AND METHODS FOR MAPPING ELECTRICAL ACTIVITY IN THE HEART

(71) Applicant: Boston Scientific Scimed Inc., Maple Grove, MN (US)

(72) Inventors: Alireza Ghodrati, Hopkinton, MA (US); Nathan H. Bennett, Cambridge, MA (US); Brian Stewart, North Reading, MA (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 319 days.

(21) Appl. No.: 16/249,162

(22) Filed: Jan. 16, 2019

(65) Prior Publication Data

US 2019/0216346 A1 Jul. 18, 2019

Related U.S. Application Data

(60) Provisional application No. 62/617,920, filed on Jan. 16, 2018.

(51) Int. Cl.
*A61B 5/04* (2006.01)
*A61B 5/042* (2006.01)
(Continued)

(52) U.S. Cl.
CPC .............. *A61B 5/341* (2021.01); *A61B 5/287* (2021.01); *A61B 5/316* (2021.01); *A61B 5/6858* (2013.01);
(Continued)

(58) Field of Classification Search
CPC ......... A61B 5/341; A61B 5/287; A61B 5/316; A61B 5/7203; A61B 5/6858; A61B 5/339; A61B 5/068; A61B 2562/0209
See application file for complete search history.

(56) References Cited

U.S. PATENT DOCUMENTS 5,546,940 A 8/1996 Panescu et al.
5,647,870 A 7/1997 Kordis et al.
(Continued)

FOREIGN PATENT DOCUMENTS

CN 1253761 A 5/2000
CN 103327887 A 9/2013
(Continued)

OTHER PUBLICATIONS

Bayly, P. V.; et al. (1998). Estimation of Conduction Velocity Vector Fields from Epicardial Mapping Data. IEEE Transactions of Biomedical Engineering, 45(5):563-571.
(Continued)

*Primary Examiner* — Mark W. Bockelman
(74) *Attorney, Agent, or Firm* — Faegre Drinker Biddle & Reath LLP

(57) ABSTRACT

A system including a catheter including multiple, spatially distributed electrodes configured to measure electrical signals of a heart, a system configured to determine a position of the electrodes at multiple, different catheter positions in the heart, and a processing unit for mapping electrical activity in the heart. The processing unit is configured to receive the measured electrical signals from each position of the multiple, different catheter positions and determine whether the measured electrical signals at the position are organized. If the measured electrical signals at the position are organized, the processing unit is configured to determine at least one of velocity vectors, cycle length, and degree of organization at the position from the measured electrical signals.

20 Claims, 8 Drawing Sheets

(51) Int. Cl.
  *A61B 5/06* (2006.01)
  *A61B 5/00* (2006.01)
  *A61B 5/044* (2006.01)
  *A61B 5/341* (2021.01)
  *A61B 5/287* (2021.01)
  *A61B 5/316* (2021.01)
  *A61B 5/339* (2021.01)

(52) U.S. Cl.
  CPC ............ *A61B 5/7203* (2013.01); *A61B 5/068* (2013.01); *A61B 5/339* (2021.01); *A61B 2562/0209* (2013.01)

(56) References Cited

U.S. PATENT DOCUMENTS

| | | |
|---|---|---|
| 5,718,241 A | 2/1998 | Ben-Haim et al. |
| 6,070,094 A | 5/2000 | Swanson et al. |
| 6,233,491 B1 | 5/2001 | Kordis et al. |
| 6,301,496 B1 | 10/2001 | Reisfeld |
| 6,600,948 B2 | 7/2003 | Ben-Haim et al. |
| 6,735,465 B2 | 5/2004 | Panescu |
| 7,515,954 B2 | 4/2009 | Harlev et al. |
| 7,869,854 B2 | 1/2011 | Shachar et al. |
| 8,103,327 B2 | 1/2012 | Harlev et al. |
| 8,103,338 B2 | 1/2012 | Harlev et al. |
| 8,428,700 B2 | 4/2013 | Harlev et al. |
| 8,447,377 B2 | 5/2013 | Harlev et al. |
| 8,577,450 B1 | 11/2013 | Chmiel et al. |
| 8,615,287 B2 | 12/2013 | Harlev et al. |
| 8,755,861 B2 | 6/2014 | Harlev et al. |
| 8,812,091 B1 | 8/2014 | Brodnick |
| 8,948,837 B2 | 2/2015 | Harlev et al. |
| 9,107,599 B2 | 8/2015 | Harlev et al. |
| 9,271,680 B2 | 3/2016 | Dubois et al. |
| 10,285,611 B1 | 5/2019 | Harlev et al. |
| 2005/0209525 A1 | 9/2005 | Bojovic et al. |
| 2012/0184863 A1 | 7/2012 | Harlev et al. |
| 2013/0253298 A1 | 9/2013 | Harlev et al. |
| 2013/0324871 A1 | 12/2013 | Dubois et al. |
| 2014/0336518 A1 | 11/2014 | Shuros et al. |
| 2015/0065836 A1 | 3/2015 | Thakur et al. |
| 2015/0119671 A1 | 4/2015 | Varma |
| 2015/0216438 A1 | 8/2015 | Bokan et al. |
| 2015/0238102 A1 | 8/2015 | Rubinstein et al. |
| 2015/0342536 A1 | 12/2015 | Kovtun et al. |
| 2016/0106376 A1 | 4/2016 | Li et al. |
| 2017/0055864 A1 | 3/2017 | Han et al. |
| 2017/0172508 A1 | 6/2017 | Hultz et al. |
| 2017/0281031 A1 | 10/2017 | Houben et al. |
| 2018/0325400 A1 | 11/2018 | Dubois et al. |
| 2019/0216347 A1 | 7/2019 | Ghodrati et al. |

FOREIGN PATENT DOCUMENTS

| | | |
|---|---|---|
| CN | 103354730 A | 10/2013 |
| CN | 104799850 A | 7/2015 |
| CN | 104883969 A | 9/2015 |
| EP | 2901953 A1 | 8/2015 |
| WO | 9520344 A1 | 8/1995 |
| WO | 9520420 A1 | 8/1995 |
| WO | 2012092016 A1 | 7/2012 |

OTHER PUBLICATIONS

Cantwell, C.D.; et al. (2015). Techniques for Automated Local Activation Time Annotation and Conduction Velocity Estimation in Cardiac Mapping. Biology in Medicine, 65:229-242, 2015.

International Preliminary Report on Patentability issued in PCT/US2016/067536, dated Jul. 5, 2018, 9 pages.

International Search Report and Written Opinion issued in PCT/US2016/067536, dated Mar. 24, 2017, 15 pages.

Masse, S. (2016). Resolving Myocardial Activation With Novel Omnipolar Electrograms. Circ Arrhythm Electrophysical, Original Article, 9:e004107, pp. 1-13.

Pappone, C.; et al. (2018). Clinical outcome of electrophysiologically guided ablation for nonparoxysmal atrial fibrillation using a novel real-time 3-dimensional mapping technique. Circ. Arrhythm. Electrophysiol., 11(e005904):1-13.

SYSTEMS AND METHODS FOR MAPPING ELECTRICAL ACTIVITY IN THE HEART

CROSS-REFERENCE TO RELATED APPLICATION

This application claims priority to Provisional Application No. 62/617,920, filed Jan. 16, 2018, which is herein incorporated by reference in its entirety.

TECHNICAL FIELD

The present disclosure relates to medical systems and methods for mapping electrical activity in the body. More specifically, the disclosure relates to systems and methods for mapping electrical activity in the heart.

BACKGROUND

Use of minimally invasive procedures, such as catheter ablation, to treat a variety of heart conditions, such as supraventricular and ventricular arrhythmias, is becoming increasingly more prevalent. Such procedures involve the mapping of electrical activity in the heart based on cardiac signals, such as at various locations on the endocardium surface, referred to as cardiac mapping, to identify the site of origin of the arrhythmia followed by a targeted ablation of the site. To perform such cardiac mapping a catheter with one or more electrodes can be inserted into the patient's heart chamber.

Conventional three-dimensional (3D) mapping techniques include contact mapping and non-contact mapping, and may employ a combination of contact and non-contact mapping. In these techniques, one or more catheters are advanced into the heart. With some catheters, once in the chamber, the catheter may be deployed to assume a 3D shape. In contact mapping, physiological signals resulting from the electrical activity of the heart are acquired with one or more electrodes located at the catheter distal tip after determining that the tip is in stable and steady contact with the endocardium surface of a particular heart chamber. In non-contact-based mapping systems, using the signals detected by the non-contact electrodes and information on chamber anatomy and relative electrode location, the system provides physiological information regarding the endocardium of the heart chamber. Location and electrical activity is usually measured sequentially on a point-by-point basis at about 50 to 200 points on the internal surface of the heart to construct an electro-anatomical depiction of the heart. The generated map may then serve as the basis for deciding on a therapeutic course of action, for example, tissue ablation, to alter the propagation of the heart's electrical activity and to restore normal heart rhythm.

In cardiac mapping of organized arrhythmias, such as atrial tachycardia, the electrical activation pattern in the heart is repeatable over time, and electrical activity measured by a catheter can be associated with electrical activity measured by a reference catheter or electrode, such as a coronary sinus (CS) reference catheter or electrode. As a result, sequential activation mapping of organized arrhythmias in the heart is possible.

In cardiac mapping of dissociated activity, such as atrial fibrillation, the electrical activation pattern is often not stable and electrical activity measured by a reference catheter or electrode, such as electrical activity measured by a CS reference catheter or electrode, may be dissociated. Thus, sequential activation mapping using a CS reference catheter or electrode may not lead to meaningful results.

SUMMARY

In an Example 1, a system, comprising: a catheter including multiple, spatially distributed electrodes configured to measure electrical signals of a heart; a system configured to determine a position of the electrodes at multiple, different catheter positions in the heart; and a processing unit. The processing unit is configured to receive the measured electrical signals from each position of the multiple, different catheter positions and determine whether the measured electrical signals at the position are organized. If the measured electrical signals at the position are organized the processing unit is configured to determine at least one of velocity vectors, cycle length, and degree of organization at the position from the measured electrical signals.

In an Example 2, the system of Example 1, wherein the processing unit is configured to determine the velocity vectors from relative activation times of the measured electrical signals at the position.

In an Example 3, the system of any of Examples 1 and 2, wherein the processing unit is configured to determine relative activation times of the measured electrical signals at the position, fit a polynomial to the relative activation times, and calculate the velocity vectors based on the polynomial and a local time gradient.

In an Example 4, the system of any of Examples 1-3, wherein the processing unit is configured to interpolate normalized velocity vectors to a mesh that represents the heart.

In an Example 5, the system of any of Examples 1-4, comprising displaying at least one of the velocity vectors, the cycle length, and the degree of organization at the position on a map of the heart to visualize the at least one of the velocity vectors, the cycle length, and the degree of organization at the position on an endocardial surface of the heart.

In an Example 6, the system of any of Examples 1-5, wherein to determine whether the measured electrical signals at the position are organized, the processing unit is configured to pre-process the measured electrical signals, detect beats in the measured electrical signals, determine an organization index based on beat interval variability, and compare the organization index to an index criteria.

In an Example 7, the system of Example 6, wherein to detect beats in the measured electrical signals, the processing unit is configured to use an adaptive threshold on the measured electrical signals to detect beats.

In an Example 8, the system of any of Examples 6 and 7, wherein to determine an organization index based on beat interval variability the processing unit is configured to determine beat interval variability of the beats in the measured electrical signals, determine number of beats that meet a beat interval variability criteria, and calculate a ratio of the number of beats that meet the beat interval variability criteria to number of detected beats.

In an Example 9, a method of mapping electrical activity in a heart, comprising: measuring electrical signals of the heart via a catheter including multiple, spatially distributed electrodes; determining a position of the electrodes at multiple, different catheter positions in the heart; measuring the electrical signals at each position of the multiple, different catheter positions; determining at each position, via a processing unit, whether the measured electrical signals are organized, and if the measured electrical signals are organized: calculating velocity vectors based on the measured electrical signals, via the processing unit.

In an Example 10, the method of Example 9, wherein determining at each position whether the measured electrical signals are organized includes pre-processing the measured electrical signals, detecting beats in the measured electrical signals via the pre-processed measured electrical signals, determining an organization index based on beat interval variability, and comparing the organization index to an index criteria.

In an Example 11, the method of Example 10, wherein detecting beats in the measured electrical signals includes comparing an adaptive threshold to the pre-processed measured electrical signals, and wherein determining an organization index based on beat interval variability includes determining beat interval variability of the beats in the measured electrical signals, determining number of beats that meet a beat interval variability criteria, and calculating a ratio of the number of beats that meet the beat interval variability criteria to number of detected beats.

In an Example 12, the method of any of Examples 9-11, wherein if the measured electrical signals are organized, the method comprises: determining relative activation times of the measured electrical signals via the processing unit; fitting a polynomial to the relative activation times via the processing unit; and calculating the velocity vectors based on the polynomial via the processing unit. Where determining relative activation times of the measured electrical signals includes: selecting beats based on organization of the measured electrical signals and the position of the electrodes in the heart; pre-processing the beats selected via low pass filtering and determining absolute value; cross-correlating pre-processed beats to neighboring pre-processed beats; and determining the relative activation times based on locations of maximum correlation. Also, where fitting a polynomial to the relative activation times includes: projecting neighboring electrodes to a plane and fitting a first order polynomial to the relative activation times.

In an Example 13, a method of mapping electrical activity in a heart, comprising: measuring electrical signals of the heart via a catheter including multiple, spatially distributed electrodes; determining a position of the electrodes at multiple, different catheter positions in the heart; measuring the electrical signals at each position of the multiple, different catheter positions; and determining at each position, via a processing unit, whether the measured electrical signals are organized. If the measured electrical signals are organized: selecting beats based on organization of the measured electrical signals and the position of the electrodes in the heart; cross-correlating selected beats to neighboring selected beats; determining relative activation times of the selected beats based on locations of maximum correlation to the neighboring selected beats; fitting a polynomial to the relative activation times; and calculating velocity vectors based on the polynomial.

In an Example 14, the method of Example 13, wherein fitting a polynomial to the relative activation times includes projecting neighboring electrodes to a plane and fitting a first order polynomial to the relative activation times.

In an Example 15, the method of any of Examples 13 and 14, wherein determining at each position whether the measured electrical signals are organized includes pre-processing the measured electrical signals, detecting beats in the measured electrical signals via the pre-processed measured electrical signals, determining an organization index based on beat interval variability, and comparing the organization index to an index criteria, and wherein determining an organization index based on beat interval variability includes determining beat interval variability of the beats in the measured electrical signals, determining number of beats that meet a beat interval variability criteria, and calculating a ratio of the number of beats that meet the beat interval variability criteria to number of detected beats.

In an Example 16, a system, comprising: a catheter including multiple, spatially distributed electrodes configured to measure electrical signals of a heart; a system configured to determine a position of the electrodes at multiple, different catheter positions in the heart; and a processing unit. The processing unit is configured to receive the measured electrical signals at each position of the multiple, different catheter positions and determine whether the measured electrical signals at the position are organized. If the measured electrical signals at the position are organized the processing unit is configured to determine at least one of velocity vectors, cycle length, and degree of organization at the position from the measured electrical signals.

In an Example 17, the system of Example 16, wherein the processing unit is configured to determine the velocity vectors from relative activation times of the measured electrical signals at the position.

In an Example 18, the system of Example 16, wherein the processing unit is configured to determine relative activation times of the measured electrical signals at the position, fit a polynomial to the relative activation times, and to calculate the velocity vectors based on the polynomial and a local time gradient.

In an Example 19, the system of Example 16, wherein the processing unit is configured to interpolate normalized velocity vectors to a mesh that represents the heart.

In an Example 20, the system of Example 16, wherein the processing unit is configured to display at least one of the velocity vectors, the cycle length, and the degree of organization at the position on a map of the heart to visualize the at least one of the velocity vectors, the cycle length, and the degree of organization at the position on an endocardial surface of the heart.

In an Example 21, the system of Example 16, wherein to determine whether the measured electrical signals at the position are organized, the processing unit is configured to pre-process the measured electrical signals, detect beats in the measured electrical signals, determine an organization index based on beat interval variability, and compare the organization index to an index criteria.

In an Example 22, the system of Example 21, wherein to detect beats in the measured electrical signals, the processing unit is configured to use an adaptive threshold on the measured electrical signals to detect beats.

In an Example 23, the system of Example 21, wherein to determine an organization index based on beat interval variability the processing unit is configured to determine beat interval variability of the beats in the measured electrical signals, determine number of beats that meet a beat interval variability criteria, and calculate a ratio of the number of beats that meet the beat interval variability criteria to number of detected beats.

In an Example 24, the system of Example 16, wherein to determine relative activation times of the measured electrical signals at the position, the processing unit is configured to: select beats based on organization of the measured electrical signals and the position of the electrodes in the heart; pre-process the beats selected via low pass filtering and determining absolute value; cross-correlate pre-processed beats to neighboring pre-processed beats; and determine the relative activation times based on locations of maximum correlation. Also, wherein to fit a polynomial to the relative activation times, the processing unit is configured to project neighboring electrodes to a plane and fit a first order polynomial to the relative activation times.

In an Example 25, a method of mapping electrical activity in a heart, comprising: measuring electrical signals of the heart via a catheter including multiple, spatially distributed electrodes; determining a position of the electrodes at multiple, different catheter positions in the heart; measuring the electrical signals at each position of the multiple, different catheter positions; and determining at each position, via a processing unit, whether the measured electrical signals are organized. If the measured electrical signals are organized: calculating velocity vectors based on the measured electrical signals, via the processing unit.

In an Example 26, the method of Example 25, comprising: displaying the velocity vectors on a map of the heart to visualize the velocity vectors on an endocardial surface of the heart.

In an Example 27, the method of Example 25, wherein determining at each position whether the measured electrical signals are organized includes pre-processing the measured electrical signals, detecting beats in the measured electrical signals via the pre-processed measured electrical signals, determining an organization index based on beat interval variability, and comparing the organization index to an index criteria.

In an Example 28, the method of Example 27, wherein detecting beats in the measured electrical signals includes comparing an adaptive threshold to the pre-processed measured electrical signals.

In an Example 29, the method of Example 27, wherein determining an organization index based on beat interval variability includes determining beat interval variability of the beats in the measured electrical signals, determining number of beats that meet a beat interval variability criteria, and calculating a ratio of the number of beats that meet the beat interval variability criteria to number of detected beats.

In an Example 30, the method of Example 25, wherein if the measured electrical signals are organized, the method comprises: determining relative activation times of the measured electrical signals, via the processing unit; fitting a polynomial to the relative activation times, via the processing unit; and calculating velocity vectors based on the measured electrical signals, via the processing unit. Also, wherein determining relative activation times of the measured electrical signals includes: selecting beats based on organization of the measured electrical signals and the position of the electrodes in the heart; pre-processing the beats selected via low pass filtering and determining absolute value; cross-correlating pre-processed beats to neighboring pre-processed beats; and determining the relative activation times based on locations of maximum correlation.

In an Example 31, the method of Example 30, wherein fitting a polynomial to the relative activation times includes projecting neighboring electrodes to a plane and fitting a first order polynomial to the relative activation times.

In an Example 32, a method of mapping electrical activity in a heart, comprising: measuring electrical signals of the heart via a catheter including multiple, spatially distributed electrodes; determining a position of the electrodes at multiple, different catheter positions in the heart; measuring the electrical signals at each position of the multiple, different catheter positions; determining at each position, via a processing unit, whether the measured electrical signals are organized. If the measured electrical signals are organized: selecting beats based on organization of the measured electrical signals and the position of the electrodes in the heart; cross-correlating selected beats to neighboring selected beats; determining relative activation times of the selected beats based on locations of maximum correlation to the neighboring selected beats; fitting a polynomial to the relative activation times; and calculating velocity vectors based on the polynomial.

In an Example 33, the method of Example 32, comprising displaying the velocity vectors on a map of the heart to visualize the velocity vectors on an endocardial surface of the heart.

In an Example 34, the method of Example 32, wherein fitting a polynomial to the relative activation times includes projecting neighboring electrodes to a plane and fitting a first order polynomial to the relative activation times.

In an Example 35, the method of Example 32, wherein determining at each position whether the measured electrical signals are organized includes pre-processing the measured electrical signals, detecting beats in the measured electrical signals via the pre-processed measured electrical signals, determining an organization index based on beat interval variability, and comparing the organization index to an index criteria, and wherein determining an organization index based on beat interval variability includes determining beat interval variability of the beats in the measured electrical signals, determining number of beats that meet a beat interval variability criteria, and calculating a ratio of the number of beats that meet the beat interval variability criteria to number of detected beats.

While multiple embodiments are disclosed, still other embodiments of the present disclosure will become apparent to those skilled in the art from the following detailed description, which shows and describes illustrative embodiments of the disclosure. Accordingly, the drawings and detailed description are to be regarded as illustrative in nature and not restrictive.

Figure 1:
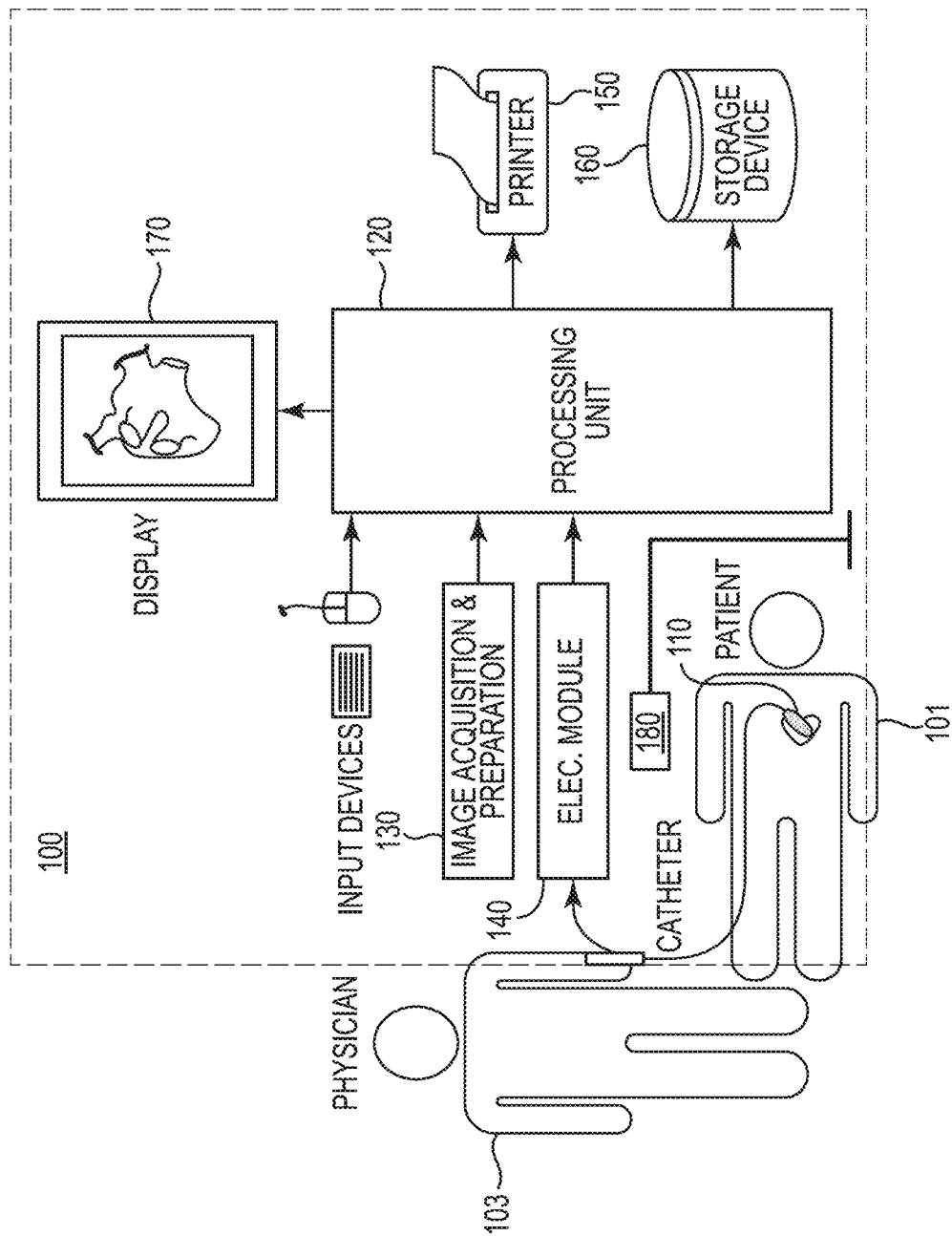
FIG. 1 is a diagram illustrating a cardiac mapping system 100, according to embodiments of the disclosure.

While the disclosure is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosure as defined by the appended claims.

DETAILED DESCRIPTION

Embodiments of systems and methods described herein facilitate processing sensed cardiac electrical signals to map and visualize dissociated electrical activity, such as atrial fibrillation, of a heart. The systems and methods provide mapping of the heart without using information gathered from a reference, such as a CS catheter. The systems and methods can use multi-electrode catheters to acquire multiple electrical signals at each position or location of the catheter in the heart. In embodiments, maps of the heart include improved visualization of dissociated electrical activity, including improved visualization of atrial fibrillation. The maps can include organizational aspects of the electrical activity in the heart, cycle length, and velocity vectors of the electrical activity on the endocardial surface. In embodiments, the systems and methods can also be used for mapping organized arrhythmias, such as atrial tachycardia.

According to embodiments, to perform aspects of embodiments of the methods described herein, cardiac electrical signals may be obtained from a mapping catheter that may be associated with a mapping system, a recording system, an ablation catheter, a memory device, such as a local memory and/or a cloud server, a communication component, a medical device, such as an implantable medical device, an external medical device, and/or a telemetry device, and/or the like.

As the term is used herein, a sensed cardiac electrical signal may refer to one or more sensed signals. Each cardiac electrical signal may include a number of intracardiac electrograms (EGMs) sensed within a patient's heart, and may include any number of features that may be ascertained by aspects of the system 100. Examples of cardiac electrical signal features include, but are not limited to, activation times, activations, activation waveforms, filtered activation waveforms, minimum voltage values, maximum voltages values, maximum negative time-derivatives of voltages, instantaneous potentials, voltage amplitudes, dominant frequencies, peak-to-peak voltages, and/or the like. A cardiac electrical signal feature may refer to one or more features extracted from one or more cardiac electrical signals, derived from one or more features that are extracted from one or more cardiac electrical signals, and/or the like. Additionally, a representation, on a cardiac and/or a surface map, of a cardiac electrical signal feature may represent one or more cardiac electrical signal features, an interpolation of a number of cardiac electrical signal features, and/or the like.

Each cardiac signal may be associated with a set of respective position coordinates that corresponds to the location at which the cardiac electrical signal was sensed. Each of the respective position coordinates for the sensed cardiac signals may include three-dimensional Cartesian coordinates, polar coordinates, and/or the like. In embodiments, other coordinate systems can be used. In embodiments, an arbitrary origin is used and the respective position coordinates refer to positions in space relative to the arbitrary origin. Since, in embodiments, the cardiac signals may be sensed on the cardiac surfaces, the respective position coordinates may be on the endocardial surface, epicardial surface, in the mid-myocardium of the patient's heart, and/or in the vicinity of one of these.

FIG. 1 is a diagram illustrating a cardiac mapping system 100, according to embodiments of the disclosure. As indicated above, embodiments of the subject matter disclosed herein may be implemented in a mapping system, such as mapping system 100, while other embodiments may be implemented in an ablation system, a recording system, a computer analysis system, and/or the like. The mapping system 100 includes a moveable catheter 110 having multiple, spatially distributed electrodes. During a signal-acquisition stage of a cardiac mapping procedure, the catheter 110 is displaced to multiple positions within the heart chamber into which the catheter 110 is inserted. In some embodiments, the distal end of the catheter 110 is fitted with multiple electrodes spread somewhat uniformly over the catheter. For example, the electrodes may be mounted on the catheter 110 following a 3D olive shape, a basket shape, and/or the like. The electrodes are mounted on a device capable of deploying the electrodes into the desired shape while inside the heart, and retracting the electrodes when the catheter is removed from the heart. To allow deployment into a 3D shape in the heart, electrodes may be mounted on a balloon, shape memory material such as Nitinol, actuable hinged structure, and/or the like. According to embodiments, the catheter 110 may be a mapping catheter, an ablation catheter, a diagnostic catheter, a CS catheter, and/or the like. For example, aspects of embodiments of the catheter 110, the electrical signals obtained using the catheter 110, and subsequent processing of the electrical signals, as described herein, may also be applicable in implementations having a recording system, ablation system, and/or any other system having a catheter with electrodes that may be configured to obtain cardiac electrical signals.

At each of the positions to which the catheter 110 is moved, the catheter's multiple electrodes acquire signals resulting from the electrical activity in the heart. Consequently, reconstructing and presenting to a user, such as a doctor and/or a technician, physiological data pertaining to the heart's electrical activity may be based on information acquired at multiple locations, thereby providing a more accurate and faithful reconstruction of physiological behavior of the endocardium surface. The acquisition of signals at multiple catheter positions in the heart chamber enables the catheter to effectively act as a "mega-catheter" whose effective number of electrodes and electrode span is proportional to the product of the number of locations in which signal acquisition is performed and the number of electrodes the catheter has.

To enhance the quality of the reconstructed physiological information at the endocardium surface, in some embodiments, the catheter 110 is moved to more than three locations, for example, more than 5, 10, or even 50 locations, within the heart chamber. Further, the spatial range over which the catheter is moved may be larger than one third (⅓)

of the diameter of the heart cavity, for example, larger than 35%, 40%, 50% or even 60% of the diameter of the heart cavity. Additionally, in some embodiments, the reconstructed physiological information is computed based on signals measured over several heart beats, either at a single catheter location within the heart chamber or over several locations.

In some embodiments, where reconstructed physiological information is based on multiple measurements over several heart beats, the measurements may be synchronized with one another so that the measurements are performed at approximately the same phase of the heart cycle. The signal measurements over multiple beats may be synchronized based on features detected from physiological data such as surface electrocardiograms (ECGs) and/or intracardiac electrograms (EGMs).

The cardiac mapping system 100 further includes a processing unit 120 which performs several of the operations pertaining to the mapping procedure, including the reconstruction procedure to determine the physiological information at the endocardium surface and/or within a heart chamber. The processing unit 120 also may perform a catheter registration procedure. The processing unit 120 also may generate a 3D grid used to aggregate the information captured by the catheter 110 and to facilitate display of portions of that information.

The position of the catheter 110 inserted into the heart chamber can be determined using a conventional sensing and tracking system 180 that provides the 3D spatial coordinates of the catheter and/or its multiple electrodes with respect to the catheter's coordinate system as established by the sensing and tracking system. These 3D spatial locations may be used in building the 3D grid. Embodiments of the system 100 may use a hybrid location technology that combines impedance location with magnetic location technology. This combination may enable the system 100 to accurately track catheters that are connected to the system 100. Magnetic location technology uses magnetic fields generated by a localization generator positioned under the patient table to track catheters with magnetic sensors. Impedance location technology may be used to track catheters that may not be equipped with a magnetic location sensor, and may utilize surface ECG patches.

In embodiments, to perform a mapping procedure and reconstruct physiological information on the endocardium surface, the processing unit 120 may align the coordinate system of the catheter 110 with the endocardium surface's coordinate system. The processing unit 110 (or some other processing component of the system 100) may determine a coordinate system transformation function that transforms the 3D spatial coordinates of the catheter's locations into coordinates expressed in terms of the endocardium surface's coordinate system, and/or vice-versa. In embodiments, such a transformation may not be necessary, as embodiments of the 3D grid described herein may be used to capture contact and non-contact EGMs, and select mapping values based on statistical distributions associated with nodes of the 3D grid. The processing unit 120 also may perform post-processing operations on the physiological information to extract and display useful features of the information to the operator of the system 100 and/or other persons (e.g., a physician).

According to embodiments, the signals acquired by the multiple electrodes of catheter 110 are passed to the processing unit 120 via an electrical module 140, which may include, for example, a signal conditioning component. The electrical module 140 may be configured to receive the signals communicated from the catheter 110 and perform signal enhancement operations on the signals before they are forwarded to the processing unit 120. The electrical module 140 may include signal conditioning hardware, software, and/or firmware that may be used to amplify, filter and/or sample intracardiac potential measured by one or more electrodes. In some embodiments, the intracardiac signals have a maximum amplitude of 60 mV, with a mean of a few millivolts. In some embodiments, the signals are pre-processed in one or more of the electrical module 140 and the processing unit 120.

In some embodiments, the signals are bandpass filtered in a frequency range, e.g., 0.5-500 Hz, and sampled with analog to digital converters, e.g., with 15-bit resolution at 1 kHz. In some embodiments the signals are bandpass filtered in a frequency range, e.g., 0.5-500 Hz, derivatives of the filtered signals are obtained, absolute values of the derivatives are obtained, and the resulting waveforms are further low pass filtered, e.g., 20 Hz.

Other types of signal processing operations, such as spectral equalization, automatic gain control, etc. may also take place. For example, in embodiments, the intracardiac signals may be unipolar signals, measured relative to a reference, which may be a virtual reference, such as, for example, a CS catheter or Wilson's Central Terminal (WCT), from which the signal processing operations may compute differences to generate multipolar signals, e.g., bipolar signals, tripolar signals, etc. The signals may be otherwise processed, e.g., filtered, sampled, etc., before and/or after generating the multipolar signals. Also, to avoid interference with electrical equipment in the room, the signal may be filtered to remove the frequency corresponding to the power supply, e.g., 60 Hz. The resultant processed signals are forwarded by the module 140 to the processing unit 120 for further processing.

In embodiments, the processing unit 120 may be configured to process the resultant processed signals. In embodiments, because the processing unit 120 may be configured to process any number of different types of electrical signals, whether they have been preprocessed or not, the terms "electrical signal(s)," "cardiac electrical signal(s)" and terms including one or more of the aforementioned, shall be understood to refer to electrical signals, processed, e.g., pre-processed, electrical signals, raw signal data, interpolated electrical signals, estimated electrical signals, and/or any other type of information representing an electrical signal, as described herein.

Embodiments of the processing unit 120 may be configured to receive a number of electrical signals such as, for example, cardiac electrical signals. The processing unit 120 may receive the electrical signals from the electrical module 140, from a memory device, from a catheter, e.g., the catheter 110, from another computing device, from a user via a user input device, and/or the like. In embodiments, the processing unit 120 may receive an indication of a measurement location corresponding to each electrical signal. The processing unit 120 may be configured to generate, based on the electrical signals, a cardiac map, which may be presented via a display device 170. In embodiments, the cardiac map includes a number of annotations representing a number of cardiac signal features, which may include, for example, one or more activation times, minimum voltage values, maximum voltage values, maximum negative time-derivatives of voltage, instantaneous potentials, voltage amplitudes, dominant frequencies, and/or peak-to-peak voltages. In embodiments, the cardiac map may include one or more of organization information related to the organization of the electrical activity in the heart, cycle length information, and velocity vector information.

In some embodiments, the mapping system 100 includes a catheter 110 that includes multiple, spatially distributed electrodes configured to measure electrical signals of the heart, and a system, such as sensing and tracking system 180, configured to determine the positions of the electrodes of the catheter 110 in the heart at multiple, different catheter positions in the heart. The processing unit 120 (and/or the electrical module 140) are configured to receive the measured electrical signals from each position of the multiple, different catheter positions and determine whether the measured electrical signals received from a position are organized. For example, for each electrode at or near the endocardium surface of the heart, such as within 2 or 3 millimeters of the endocardium surface, an interval of the measured electrical signals, such as 2.5 seconds, is selected and processed to determine if the electrical activity at the position is organized activity. If the electrical activity at the position is organized, the processing unit 120 is configured to determine relative activation times of the measured electrical signals at the position from neighboring electrodes, fit a polynomial to the relative activation times, and calculate velocity vectors based on the polynomial. In some embodiments, the processing unit also calculates cycle length of the measured signals.

In some embodiments, the processing unit 120 is configured to facilitate display, via display device 170, of the cardiac map. In embodiments, the display may include any number of different types of parameters, settings, and/or the like that may be configured to change one or more features of an appearance of a displayed representation. For example, in embodiments, display parameters may include brightness, contrast, color saturation, sharpness, and/or the like. Thus, in embodiments, the map includes multiple colors and/or colored regions, where color saturation values, relative color saturation values, and/or the like, may be adjustable via user input, an algorithm, and/or the like. In some embodiments, the resulting map visualized on display 170 includes organization information for different positions in the heart, cycle lengths, and velocity vectors characterizing the electrical activity on the endocardial surface of the heart.

As further shown in FIG. 1, the cardiac mapping system 100 may include peripheral devices such as a printer 150 and/or display device 170, both of which may be interconnected to the processing unit 120. Additionally, the mapping system 100 includes storage device 160 that may be used to store data acquired by the various interconnected modules, including the volumetric images, raw data measured by electrodes and/or the resultant endocardium representation computed therefrom, the partially computed transformations used to expedite the mapping procedures, the reconstructed physiological information corresponding to the endocardium surface, and/or the like.

In embodiments, the processing unit 120 may be configured to automatically improve the accuracy of its algorithms by using one or more artificial intelligence, i.e., machine-learning, techniques, classifiers, and/or the like. In embodiments, for example, the processing unit 120 may use one or more supervised and/or unsupervised techniques such as, for example, support vector machines (SVMs), k-nearest neighbor techniques, artificial neural networks, and/or the like. In embodiments, classifiers may be trained and/or adapted using feedback information from a user, other metrics, and/or the like.

The illustrative cardiac mapping system 100 shown in FIG. 1 is not intended to suggest any limitation as to the scope of use or functionality of embodiments of the present disclosure. Neither should the illustrative cardiac mapping system 100 be interpreted as having any dependency or requirement related to any single component or combination of components illustrated therein. Additionally, various components depicted in FIG. 1 may be, in embodiments, integrated with various ones of the other components depicted therein (and/or components not illustrated), all of which are considered to be within the ambit of the subject matter disclosed herein. For example, the electrical module 140 may be integrated with the processing unit 120. Additionally, or alternatively, aspects of embodiments of the cardiac mapping system 100 may be implemented in a computer analysis system configured to receive cardiac electrical signals and/or other information from a memory device, e.g., a cloud server, a mapping system memory, etc., and perform aspects of embodiments of the methods described herein for processing cardiac information, e.g., determining annotation waveforms, etc. That is, for example, a computer analysis system may include a processing unit 120, but not a mapping catheter.

Figure 2A:
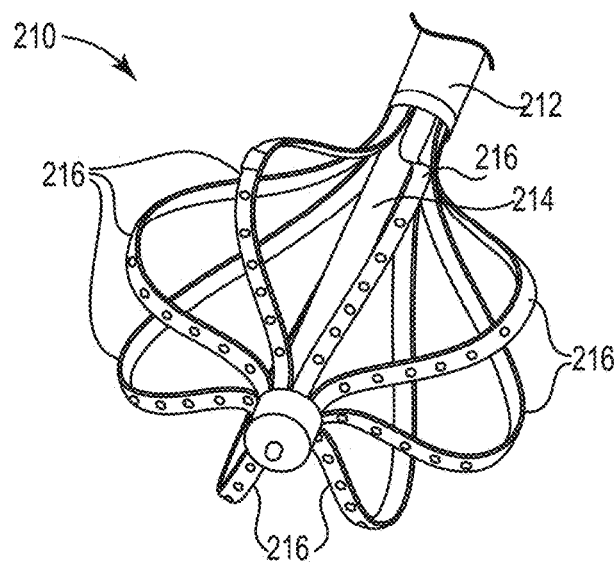
FIG. 2A is a diagram illustrating a perspective view of a catheter 210, according to embodiments of the disclosure.
Figure 2B:
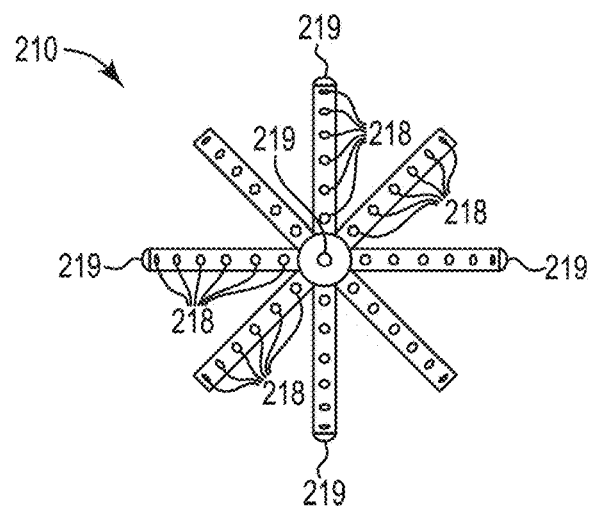
FIG. 2B is a diagram illustrating an end view of the catheter 210, according to embodiments of the disclosure.
Figure 2C:
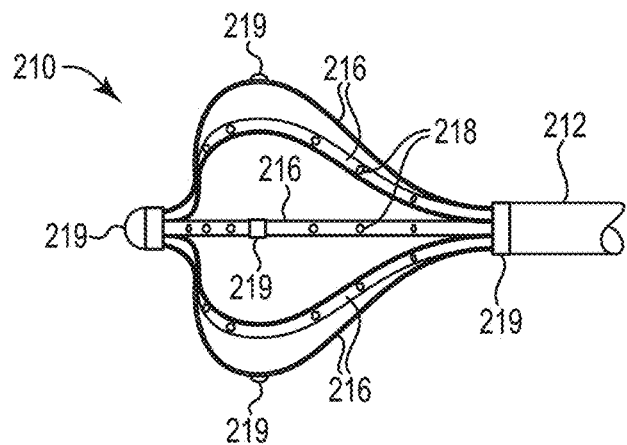
FIG. 2C is a diagram illustrating a side view of the catheter 210, according to embodiments of the disclosure.

FIGS. 2A-2C are diagrams illustrating different views of a catheter 210, according to embodiments of the disclosure. FIG. 2A is a diagram illustrating a perspective view of the catheter 210, according to embodiments of the disclosure. FIG. 2B is a diagram illustrating an end view of the catheter 210, according to embodiments of the disclosure. FIG. 2C is a diagram illustrating a side view of the catheter 210, according to embodiments of the disclosure. In some embodiments, the catheter 210 is one example of catheter 110 (shown in FIG. 1).

Catheter 210 includes a base sleeve 212, a central retractable inner member 214, and multiple splines 216 connected to base sleeve 212 at one end and inner member 214 at the other end. When inner member 214 is in an extended configuration or position (not shown), the splines 216 are pulled tight to the inner member 214 so that catheter 210 has a narrow profile for guiding it through blood vessels. When inner member 214 is retracted, as shown in FIGS. 2A-2C, the splines 216 are deployed and pushed into an outward "olive" shaped configuration for use in the heart cavity. The splines 216 each carry multiple electrodes, such that with the inner member 214 in the retracted configuration, the electrodes are deployed in the sense that they are distributed over a greater volume.

A large number of potential measuring electrodes (PME) 218 are mounted on catheter 210 to measure electrical signals, such as cardiac electrical signals generated by the heart. Also, a number, such as greater than 6, current injecting electrodes (CIE) 219 are mounted on catheter 210 to inject current into the heart. For example, 3 orthogonal CIE pairs may be mounted on the catheter 210, where each CIE pair defines a source and a sink electrode, respectively, for injecting current into the heart cavity.

It should be noted that a low impedance electrode can be used for current injection and in a case where many or all electrodes are capable of injecting current the designation of such electrodes as CIE on the catheter only indicates that these electrodes are actually being used for current injection. Also, it should be further appreciated that other configuration sets of CIE are possible as long as these configurations are known and can be accounted for. Examples of such configurations could be quadruples involving 4 CIE, or even a non-symmetrical configuration involving 3 CIE in known positions on the catheter. Also, configurations other than orthogonal pairs may be used for either method, and more than 2 CIE 219 may participate in current injection at a given time.

Figure 3:
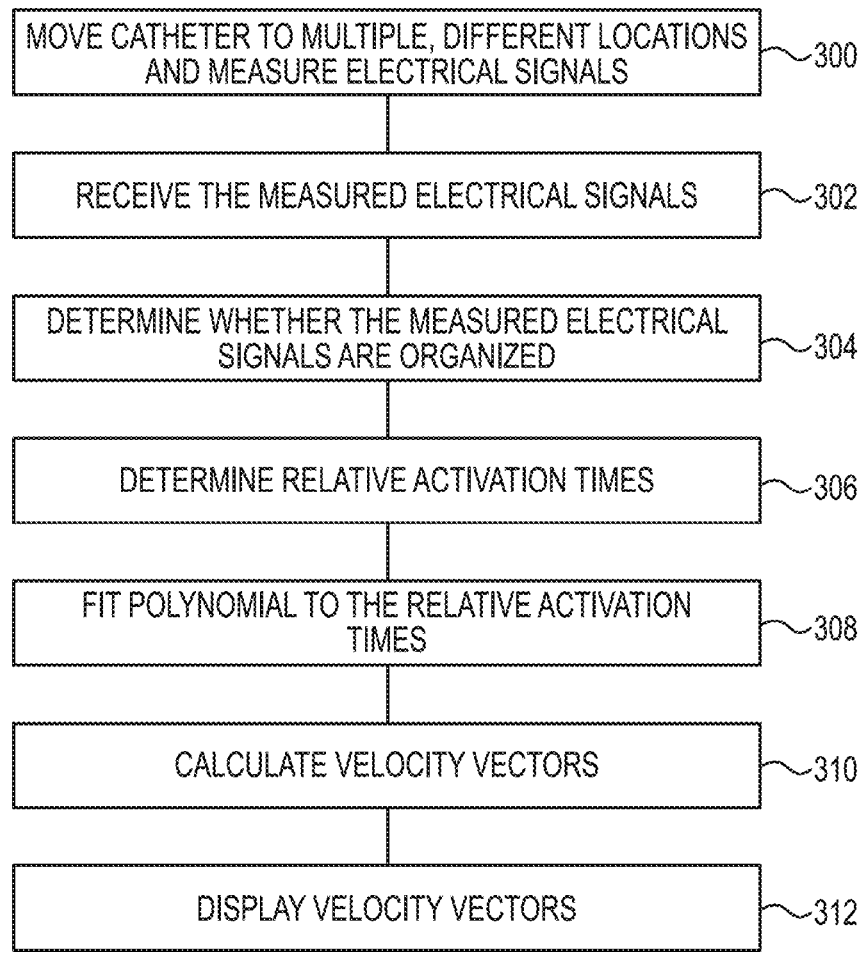
FIG. 3 is a flow chart diagram illustrating a process for mapping and visualizing sensed electrical activity in the heart, according to embodiments of the disclosure.

FIG. 3 is a flow chart diagram illustrating a process for mapping and visualizing sensed electrical activity in the heart, according to embodiments of the disclosure. The process can be performed by the cardiac mapping system 100 and used to map and visualize dissociated electrical activity, such as atrial fibrillation, and organized electrical activity, such as atrial tachycardia. The process is performed without using information gathered from a reference, such as a CS catheter.

The cardiac mapping system 100 includes the catheter 110, which has multiple, spatially distributed electrodes configured to measure electrical signals of the heart, and a sensing and tracking system, such as sensing and tracking system 180, that provides 3D spatial coordinates of the catheter 110 and its multiple electrodes with respect to the catheter's coordinate system. The sensing and tracking system is configured to determine the positions of the catheter electrodes at multiple, different catheter positions in the heart. In some embodiments, the cardiac mapping system 100 includes the catheter 210 of FIGS. 2A-2C.

The cardiac mapping system 100 also includes the processing unit 120 that provides processing power and electronic circuits for receiving and processing the measured electrical signals. In some embodiments, the processing unit 120 can determine a coordinate system transformation function that transforms the 3D spatial coordinates of the catheter and electrode locations in the catheter's coordinate system into coordinates expressed in terms of the endocardium surface's coordinate system. In some embodiments, the processing unit 120 includes the electrical module 140.

At 300, the catheter 110 is inserted into the heart of the patient and moved to multiple, different locations in the heart. The multiple, spatially distributed electrodes of the catheter 110 measure electrical signals generated by the heart at each of the multiple, different locations in the heart. The sensing and tracking system determines the locations of the electrodes in the heart at each of the multiple, different locations in the heart and the processing unit 120 determines the locations of the electrodes at each of the multiple, different locations in the heart in relation to the endocardium surface of the heart.

At 302, the processing unit 120, which may include the electrical module 140, receives the measured electrical signals acquired by the multiple electrodes of the catheter 110 at each location of the multiple, different catheter locations. At 304, the processing unit 120 determines whether the measured electrical signals are organized at each of the multiple, different catheter locations.

If the measured electrical signals at a location of the multiple, different catheter locations are organized, the processing unit 120 determines at least one of velocity vectors, cycle length(s), and the degree of organization, which may be the organization index value, at the position based on or from the measured electrical signals. In some embodiments, the processing unit is configured to determine the velocity vectors from relative activation times of the measured electrical signals at the position. In some embodiments, the processing unit is configured to interpolate normalized velocity vectors to a mesh that represents the heart.

In some embodiments, the processing unit is configured to determine relative activation times of the measured electrical signals at the position, fit a polynomial to the relative activation times, and calculate the velocity vectors based on the polynomial and a local time gradient. At 306 the processing unit 120 determines relative activation times of the measured electrical signals at the location. At 308 the processing unit 120 fits a polynomial to the relative activation times, and at 310 the processing unit 120 calculates velocity vectors based on the polynomial.

In some embodiments, as indicated at 312, the processing unit 120 displays the velocity vectors on a map of the heart, such as on display 170, to visualize the velocity vectors on the endocardium surface of the heart. In some embodiments, the processing unit is configured to display at least one of the velocity vectors, the cycle length, and the degree of organization at the position on a map of the heart to visualize the at least one of the velocity vectors, the cycle length, and the degree of organization at the position on an endocardial surface of the heart.

Figure 4:
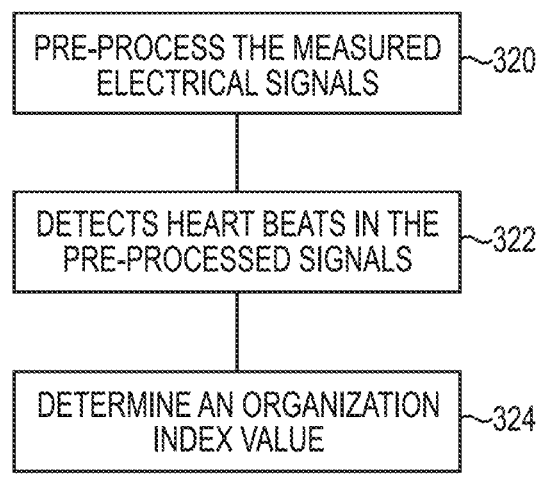
FIG. 4 is a flow chart diagram illustrating a process to determine whether the measured electrical signals at the position are organized, according to embodiments of the disclosure.

FIG. 4 is a flow chart diagram illustrating a process to determine whether the measured electrical signals at the position are organized, according to embodiments of the disclosure. This process can be performed by the cardiac mapping system 100, including the processing unit 120.

At 320, the processing unit 120, which may include the electrical module 140, pre-processes the measured electrical signals. In some embodiments, in pre-processing, the processing unit 120 provides one or more of: the processing unit 120 low pass filters the measured electrical signals to filter out high frequency noise, the processing unit 120 determines the derivatives of the low pass filtered signal, the processing unit 120 determines an absolute value of the derivatives of the low pass filtered signal to make the processed signals positive, and then, optionally, the processing unit 120 low pass filters the derivatives to remove high frequency artifacts.

At 322, the processing unit 120 detects heart beats in the pre-processed signals. In some embodiments, the processing unit 120 provides an adaptive threshold beat detection process for identifying beats and finding the threshold value that identifies beats and signals that are the most organized.

In some embodiments, the adaptive threshold process includes starting with a threshold value equal to some value, such as one half, of the highest electrical signal value. The threshold value is compared to the pre-processed signal and points on the signal that meet or exceed the threshold value are identified as beat signals that indicate the beginning/ending of a beat. In this process, a 50 millisecond refractory period is provided around each identified beat signal for ignoring other possible beat signals and/or ignoring an upward change in the observed signal. Next, the beat intervals between adjacent beat signals are determined and, at 324, an organization index value is determined for the measured electrical signals.

In the adaptive threshold process, after each threshold value is processed to identify beat signals, the threshold value is adjusted and the process repeated. For, example, in an iterative process, the threshold value may be adjusted to one third, then one fourth, then one sixth, and then one eighth of the highest signal value, where intervals between adjacent beat signals are determined and an organization index is calculated for each of the different threshold values. The threshold value that provides the highest organization index value provides the most organized set of beat signals and intervals and used for further processing of the signals and determining the velocity vectors.

At 324, the processing unit 120 determines the organization index for each of the different threshold values. In embodiments, the processing unit determines the organization index value based on variability of beat intervals. For example, beat interval variability can be determined by subtracting a next beat interval value from the current beat interval value and dividing the subtraction result by the current beat interval value. The resulting value is the beat interval variability of the current beat interval. In some embodiments, the absolute value of the resulting value is the beat interval variability of the current beat interval.

Next, for a given length of the measured electrical signal, such as 2.5 seconds, determine the number of beat intervals that have a beat interval variability of less than a certain percentage, such as 15 percent. Also, in some embodiments, to be counted, each of the beat intervals should be between 100 milliseconds and 400 milliseconds in length.

Next, if at least a given number of beat intervals, such as eight beat intervals, in the measured electrical signal have a beat interval variability of less than the certain percentage, such as 15 percent, an organization index value is determined. The organization index value is calculated to be equal to the number of beat intervals with a beat interval variability of less than the percentage, such as 15 percent, divided by the total number of beat intervals detected in the sample of the measured electrical signal.

Next, the organization index value is compared to an organization index threshold or criteria to determine if the measured electrical signal is organized. In some embodiments, the organization index threshold or criteria is 0.6 or 60%. In some embodiments, the cycle length is determines, where in some embodiments the cycle length is determined to be the median of the beat intervals that have a beat interval variability of less than the certain percentage, such as 15 percent.

Figure 5A:
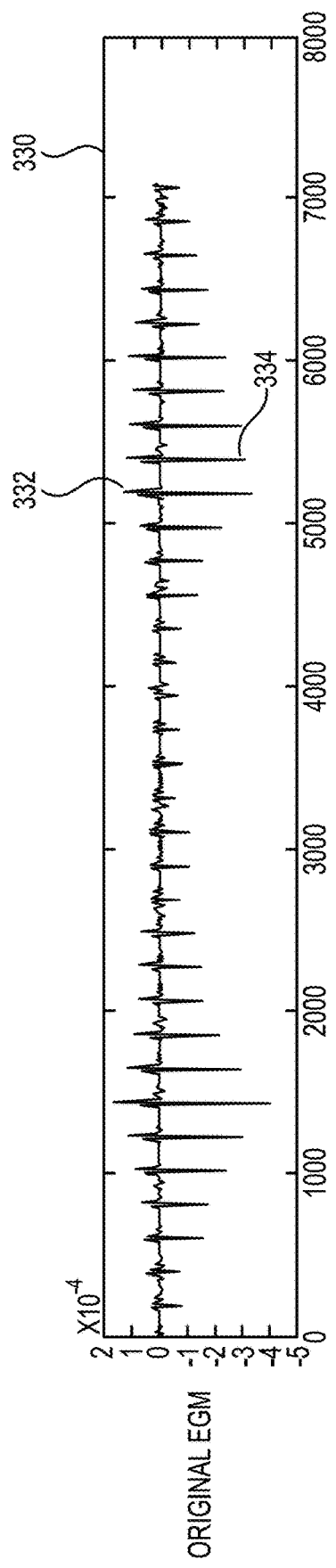
FIG. 5A is a diagram illustrating an original electrogram 330 of one of the measured electrical signals prior to pre-processing the measured electrical signal, according to embodiments of the disclosure.

FIG. 5A is a diagram illustrating an original electrogram 330 of one of the measured electrical signals prior to pre-processing the measured electrical signal, according to embodiments of the disclosure. The original electrogram 330 includes values that are greater than zero at 332 and less than zero at 334. In addition, the original electrogram 330 includes a number of high frequency components, which may make it difficult to detect beat signals.

In embodiments, the original electrogram 330 is low pass filtered to remove or reduce high frequency noise. The processing unit 120 then determines the derivative of the low pass filtered signal and an absolute value of the derivative to make the processed signal positive. The absolute value of the derivative is then low pass filtered to further remove or reduce high frequency artifacts.

Figure 5B:
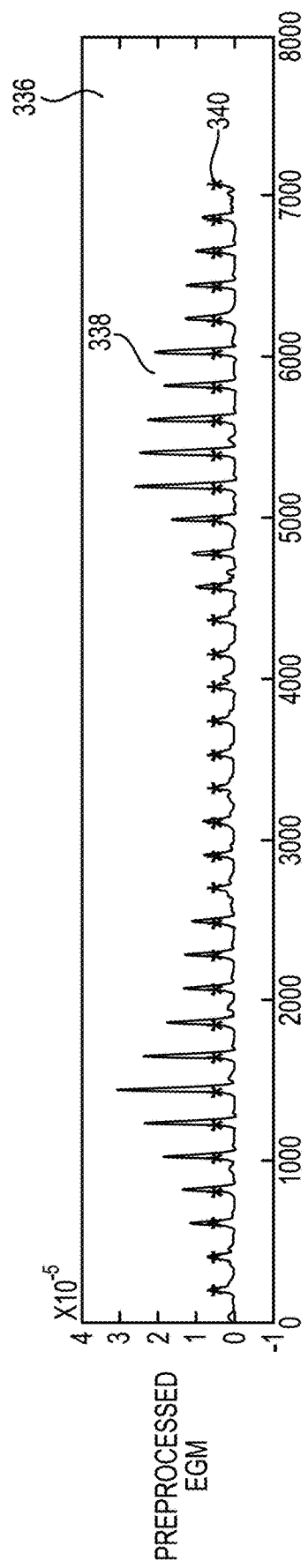
FIG. 5B is a diagram illustrating a pre-processed electrogram 336, according to embodiments of the disclosure.

The resulting signal is illustrated in FIG. 5B, which is a diagram illustrating a pre-processed electrogram 336, according to embodiments of the disclosure. The pre-processed electrogram includes positive values at 338, where threshold values 340 can be compared to the pre-processed electrogram 336 to determine beat signals and beat intervals for determining the organization index value for the measured electrical signal.

Figure 6:
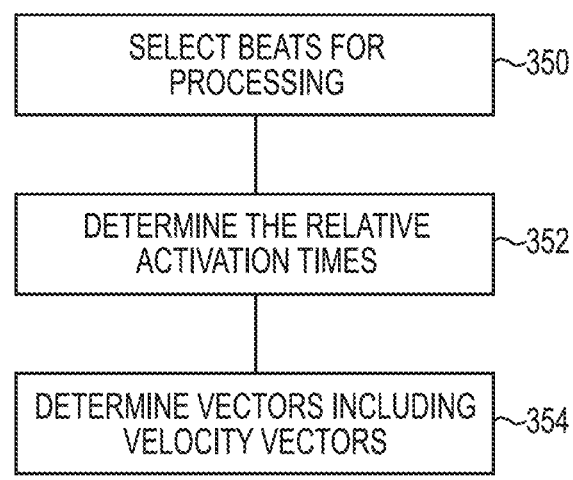
FIG. 6 is a flow chart diagram illustrating a process for determining relative activation times of the measured electrical signals and for determining vectors, such as propagation vectors and velocity vectors, at locations of the multiple, different catheter locations, according to embodiments of the disclosure.

FIG. 6 is a flow chart diagram illustrating a process for determining relative activation times of the measured electrical signals and for determining vectors, such as propagation vectors and velocity vectors, at locations of the multiple, different catheter locations, according to embodiments of the disclosure.

At 350, the processing unit 120 selects beats for processing. Beats are selected based on one or more of the following criteria: the organization index value of the measured electrical signals that measured the beat; the number of electrodes that measured the beat and the positions of the electrodes in relation to the endocardium surface of the heart; and the positions of the electrodes that measured the beat in relation to one another on the splines of the catheter.

In some embodiments, a beat must meet all of the above criteria before being selected for processing.

In some embodiments, to select a beat, the organization index value of the measured electrical signals of the beat must be greater than an organization index threshold value. In some embodiments the organization index threshold is 0.6 or 60%.

In some embodiments, to select a beat, the beat must be measured by at least a certain number of electrodes, such as 4 electrodes, and the electrodes must be within a certain distance, such as 3 millimeters, of the endocardium surface of the heart. This ensures the quality and integrity of the measured electrical signals.

In some embodiments, to select a beat, the electrodes that measured the beat must be on at least two splines of the catheter, such as catheter 210 of FIGS. 2A-2C. In some embodiments, to select a beat, the electrodes that measured the beat must be on at least two neighboring or adjacent splines of the catheter, such as catheter 210 of FIGS. 2A-2C.

At 352, the processing unit 120 determines the relative activation times at the electrodes that measured the beat. To determine the relative activation times, the processing unit 120 selects an electrogram interval around the selected beat for processing. In some embodiments, the processing unit 120 selects an electrogram interval of plus 75 milliseconds and minus 75 milliseconds around the beat.

Then, the processing unit 120 evaluates the measured electrical signals or electrograms of the beat to reduce or eliminate the number of noisy electrograms, and the processing unit 120 pre-processes the electrograms. In some embodiments, the processing unit 120 pre-processes the electrograms similar to the pre-processing of the measured electrical signals described above. The processing unit 120 performs one or more of: the processing unit 120 low pass filters the electrograms to filter out high frequency noise, the processing unit 120 determines the derivatives of the low pass filtered signal, the processing unit 120 determines an absolute value of the derivatives of the low pass filtered signal to make the processed signals positive, and, optionally, the processing unit 120 low pass filters the derivatives to remove high frequency artifacts. In some embodiments, the processing unit 120 performs all of the above steps in pre-processing the electrograms. In some embodiments, the processing unit 120 also removes the baseline of the electrograms.

Next, to determine the relative activation times, the processing unit 120 cross-correlates each of the pre-processed signals to each of the other neighboring pre-processed signals. The cross-correlation waveforms are evaluated, such as by the processing unit 120, to eliminate not useful or bad cross-correlation results, which may be cross-correlations that do not show a maximum or high correlation value. The cross-correlations are provided with respect to time, such that the location of the maximum correlation between two signals indicates the relative activation time between the two electrodes that measured the signals. In some embodiments, the processing unit 120 cross-correlates at least 4 signals from at least 4 electrodes that measured the selected beat.

At 354, the processing unit 120 determines vectors, such as propagation vectors and velocity vectors, at locations of the multiple, different catheter locations. First, the processing unit 120 projects the electrodes from the catheter, such as catheter 110 or catheter 210, onto a two-dimensional plane, where the processing unit 120 can also project the relative activations times of at least some of the electrodes onto the two-dimensional plane. The processing unit 120 then fits a polynomial, such as a first order polynomial, to the relative activation times. Based on the time gradients as depicted by the polynomial, the processing unit 120 calculates one or more of propagation vectors that are normalized and show the direction of propagation of the electrical activity and velocity vectors that indicate an amplitude or magnitude of the velocity vector and the direction of the activation of the electrical activity.

Figure 7:
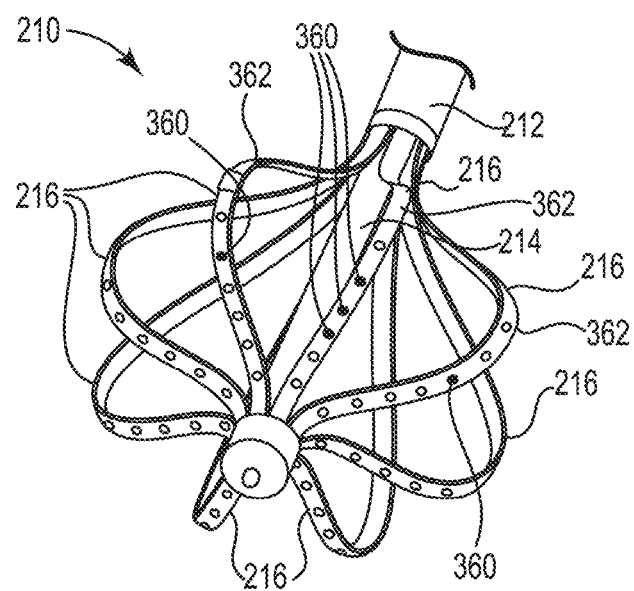
FIG. 7 is a diagram illustrating catheter 210 having five electrodes 360 on three different splines 362, which measure the electrical signals of a beat of interest, according to embodiments of the disclosure.

FIG. 7 is a diagram illustrating catheter 210 having five electrodes 360 on three different splines 362, which measure the electrical signals of a beat of interest, according to embodiments of the disclosure. In this example, each of the five electrodes 360 is 1.5-2.5 millimeters from the endocardium surface when it measures the electrical signal of the heart. Also, the organization index value of the measured electrical signals has been found to be 70%.

In this example, the criteria for selection of a beat are as follows: the organization index value of the measured electrical signals that measured the beat must be greater than the organization index threshold of 60%; the beat must be measured by at least 4 electrodes that are within 3 millimeters of the endocardium surface of the heart; and the electrodes that measure the beat must be on at least two neighboring or adjacent splines of the catheter 210.

As described above, the organization index value of the measured electrical signals was found to be 70%, which satisfies the organization index threshold of 60%. Further, the electrical signals of the beat were measured by five different electrodes 360, which satisfies the number of electrodes criteria of at least 4 electrodes. Also, each of the five electrodes 360 was 1.5-2.5 millimeters from the endocardium surface of the heart, which satisfies the measuring distance criteria of being within 3 millimeters of the endocardium surface. In addition, the electrodes 360 are located on three different splines 304, where each of the splines is adjacent to or neighboring one of the other splines 304, which satisfies the at least two different neighboring spline criteria.

Thus, the five electrodes 360 on three different splines 362 that measure the electrical signals of the beat of interest, in this example, satisfy the criteria for selection of a beat, such that the beat is selected by the processing unit 120.

Figure 8:
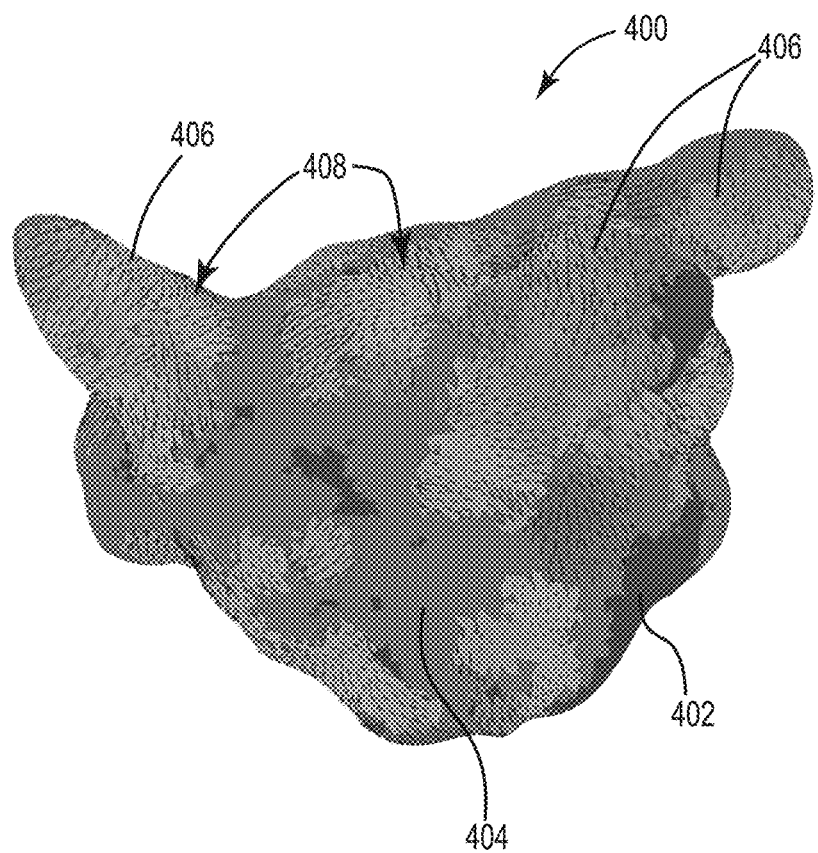
FIG. 8 is a diagram illustrating a map 400 for visualizing the organization of the electrical activity in the heart and the velocity vectors on the endocardial surface of the heart, according to embodiments of the disclosure.

FIG. 8 is a diagram illustrating a map 400 for visualizing the organization of the electrical activity in the heart and the velocity vectors on the endocardial surface of the heart, according to embodiments of the disclosure. In some embodiments, the processing unit 120 displays the map 400, including the velocity vectors, on a display such as display 170 to visualize the organization and the velocity vectors on the endocardium surface of the heart.

In the map 400: the dark gray or black areas 402 indicate areas where no data is available and the light or clear areas 404 indicate areas that are not organized. The remaining areas 406 are organized, such that the remaining areas 406 meet the organization index threshold criteria for being organized, such as 60%. The remaining areas 406 have velocity vector arrows (or velocity vectors) in them.

The remaining areas 406 may be shaded different colors or otherwise distinguished to indicate different cycle lengths of the electrical activity. For example, the remaining areas 406 may be shaded on a continuous scale form purple to blue to green to yellow to indicate cycle lengths ranging from 80 milliseconds to 200 milliseconds, respectively.

The remaining areas 406 include velocity vector arrows, see generally 408. The direction of the velocity vector arrows indicates the direction of propagation of the electrical activity, and the amplitude or magnitude of the velocity vector arrows reflect the agreement of the local velocity vectors and the confidence in and stability of the cardiac rhythm. Also, the magnitude of the velocity vectors and cycle length variability indicate the local stability of the cardiac rhythm.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:
1. A system, comprising:
a catheter including multiple, spatially distributed electrodes configured to measure electrical signals of a heart;
a system configured to determine a position of the electrodes at multiple, different catheter positions in the heart; and
a processing unit configured to receive the measured electrical signals at each position of the multiple, different catheter positions and determine whether the measured electrical signals at the position are organized, if the measured electrical signals at the position are organized the processing unit is configured to determine at least one of velocity vectors, cycle length, and degree of organization at the position from the measured electrical signals.

2. The system of claim 1, wherein the processing unit is configured to determine the velocity vectors from relative activation times of the measured electrical signals at the position.

3. The system of claim 1, wherein the processing unit is configured to determine relative activation times of the measured electrical signals at the position, fit a polynomial to the relative activation times, and to calculate the velocity vectors based on the polynomial and a local time gradient.

4. The system of claim 1, wherein the processing unit is configured to interpolate normalized velocity vectors to a mesh that represents the heart.

5. The system of claim 1, wherein the processing unit is configured to display at least one of the velocity vectors, the cycle length, and the degree of organization at the position on a map of the heart to visualize the at least one of the velocity vectors, the cycle length, and the degree of organization at the position on an endocardial surface of the heart.

6. The system of claim 1, wherein to determine whether the measured electrical signals at the position are organized, the processing unit is configured to pre-process the measured electrical signals, detect beats in the measured electrical signals, determine an organization index based on beat interval variability, and compare the organization index to an index criteria.

7. The system of claim 6, wherein to detect beats in the measured electrical signals, the processing unit is configured to use an adaptive threshold on the measured electrical signals to detect beats.

8. The system of claim 6, wherein to determine an organization index based on beat interval variability the processing unit is configured to determine beat interval variability of the beats in the measured electrical signals, determine number of beats that meet a beat interval variability criteria, and calculate a ratio of the number of beats that meet the beat interval variability criteria to number of detected beats.

9. The system of claim 1, wherein:
to determine relative activation times of the measured electrical signals at the position, the processing unit is configured to:
select beats based on organization of the measured electrical signals and the position of the electrodes in the heart;
pre-process the beats selected via low pass filtering and determining absolute value;
cross-correlate pre-processed beats to neighboring pre-processed beats; and
determine the relative activation times based on locations of maximum correlation; and
to fit a polynomial to the relative activation times, the processing unit is configured to:
project neighboring electrodes to a plane; and
fit a first order polynomial to the relative activation times.

10. A method of mapping electrical activity in a heart, comprising:
measuring electrical signals of the heart via a catheter including multiple, spatially distributed electrodes;
determining a position of the electrodes at multiple, different catheter positions in the heart;
measuring the electrical signals at each position of the multiple, different catheter positions; and
determining at each position, via a processing unit, whether the measured electrical signals are organized, and if the measured electrical signals are organized:
calculating velocity vectors based on the measured electrical signals, via the processing unit.

11. The method of claim 10, comprising:
displaying the velocity vectors on a map of the heart to visualize the velocity vectors on an endocardial surface of the heart.

12. The method of claim 10, wherein determining at each position whether the measured electrical signals are organized includes pre-processing the measured electrical signals, detecting beats in the measured electrical signals via the pre-processed measured electrical signals, determining an organization index based on beat interval variability, and comparing the organization index to an index criteria.

13. The method of claim 12, wherein detecting beats in the measured electrical signals includes comparing an adaptive threshold to the pre-processed measured electrical signals.

14. The method of claim 12, wherein determining an organization index based on beat interval variability includes determining beat interval variability of the beats in the measured electrical signals, determining number of beats that meet a beat interval variability criteria, and calculating a ratio of the number of beats that meet the beat interval variability criteria to number of detected beats.

15. The method of claim 10, wherein if the measured electrical signals are organized, the method comprises:
determining relative activation times of the measured electrical signals, via the processing unit;
fitting a polynomial to the relative activation times, via the processing unit; and
calculating velocity vectors based on the measured electrical signals, via the processing unit,
wherein determining relative activation times of the measured electrical signals includes:
selecting beats based on organization of the measured electrical signals and the position of the electrodes in the heart;
pre-processing the beats selected via low pass filtering and determining absolute value;
cross-correlating pre-processed beats to neighboring pre-processed beats; and
determining the relative activation times based on locations of maximum correlation.

16. The method of claim 15, wherein fitting a polynomial to the relative activation times includes projecting neighboring electrodes to a plane and fitting a first order polynomial to the relative activation times.

17. A method of mapping electrical activity in a heart, comprising:
measuring electrical signals of the heart via a catheter including multiple, spatially distributed electrodes;
determining a position of the electrodes at multiple, different catheter positions in the heart;
measuring the electrical signals at each position of the multiple, different catheter positions;
determining at each position, via a processing unit, whether the measured electrical signals are organized, and if the measured electrical signals are organized:
selecting beats based on organization of the measured electrical signals and the position of the electrodes in the heart;
cross-correlating selected beats to neighboring selected beats;
determining relative activation times of the selected beats based on locations of maximum correlation to the neighboring selected beats;
fitting a polynomial to the relative activation times; and
calculating velocity vectors based on the polynomial.

18. The method of claim 17, comprising:
displaying the velocity vectors on a map of the heart to visualize the velocity vectors on an endocardial surface of the heart.

19. The method of claim 17, wherein fitting a polynomial to the relative activation times includes projecting neighboring electrodes to a plane and fitting a first order polynomial to the relative activation times.

20. The method of claim 17, wherein determining at each position whether the measured electrical signals are organized includes pre-processing the measured electrical signals, detecting beats in the measured electrical signals via the pre-processed measured electrical signals, determining an organization index based on beat interval variability, and comparing the organization index to an index criteria, and wherein determining an organization index based on beat interval variability includes determining beat interval variability of the beats in the measured electrical signals, determining number of beats that meet a beat interval variability criteria, and calculating a ratio of the number of beats that meet the beat interval variability criteria to number of detected beats.

* * * * *